US012090076B2

(12) United States Patent
Nolan et al.

(10) Patent No.: US 12,090,076 B2
(45) Date of Patent: Sep. 17, 2024

(54) DEVICES AND RELATED METHODS FOR GASTRECTOMIES

(71) Applicant: Boston Scientific Scimed, Inc., Maple Grove, MN (US)

(72) Inventors: Damien V. Nolan, Craughwell (IE); Martyn G. Folan, Loughrea (IE); Matthew Montague, Galway (IE); David Burke, Tuam (IE); Enda Connaughton, Craughwell (IE); Michael Walsh, Rosscahill (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 912 days.

(21) Appl. No.: 15/606,520

(22) Filed: May 26, 2017

(65) Prior Publication Data

US 2017/0340467 A1  Nov. 30, 2017

Related U.S. Application Data

(60) Provisional application No. 62/343,502, filed on May 31, 2016.

(51) Int. Cl.
*A61B 18/14* (2006.01)
*A61F 5/00* (2006.01)
(Continued)

(52) U.S. Cl.
CPC ........ *A61F 5/0076* (2013.01); *A61B 18/1442* (2013.01); *A61B 18/1485* (2013.01);
(Continued)

(58) Field of Classification Search
CPC .. A61F 5/0076; A61F 5/0086; A61B 18/1442; A61B 18/1485;
(Continued)

(56) References Cited

U.S. PATENT DOCUMENTS 5,599,350 A * 2/1997 Schulze ............. A61B 18/1442
606/171
7,361,180 B2 * 4/2008 Saadat ............... A61B 17/0401
606/139
(Continued)

FOREIGN PATENT DOCUMENTS

EP  2 870 919 A1  5/2015

OTHER PUBLICATIONS

David Kim, "Inverted Gastric Sleeve," last accessed on Mar. 18, 2016 (7 pages).
(Continued)

*Primary Examiner* — Eun Hwa Kim
*Assistant Examiner* — Catherine Premraj
(74) *Attorney, Agent, or Firm* — Bookoff McAndrews, PLLC

(57) ABSTRACT

According to one aspect, an apparatus for treating tissue may include an elongate tube. The elongate tube may include a slot extending longitudinally along a first side of the elongate tube, a first elongate jaw member on a first side of the slot, and a second elongate jaw member on a second side of the slot. The apparatus may also include a shaft coupled to the elongate tube along a second side of the elongate tube. The first elongate jaw member may be movably coupled to the shaft, such that the first elongate jaw member may be movable toward the second elongate jaw member to converge tissue walls within the slot and cut the tissue walls within the slot.

13 Claims, 7 Drawing Sheets

(51) Int. Cl.
*A61B 17/00* (2006.01)
*A61B 17/30* (2006.01)
*A61B 18/00* (2006.01)

(52) U.S. Cl.
CPC .. *A61F 5/0086* (2013.01); *A61B 2017/00876* (2013.01); *A61B 2017/306* (2013.01); *A61B 2018/00494* (2013.01); *A61B 2018/00607* (2013.01); *A61B 2018/1452* (2013.01)

(58) Field of Classification Search
CPC .... A61B 2017/00876; A61B 2017/306; A61B 2018/00494; A61B 2018/00607; A61B 2018/1452; A61B 17/00; A61B 17/28; A61B 2018/142; A61B 18/1445; A61B 2017/1125; A61B 2017/113; A61B 17/115; A61B 17/1155
See application file for complete search history.

(56) References Cited

U.S. PATENT DOCUMENTS

| | | | |
|---|---|---|---|
| 7,779,845 B2 * | 8/2010 | Ortiz | A61B 17/0218 |
| | | | 128/898 |
| 7,896,894 B2 | 3/2011 | Ortiz et al. | |
| 8,137,367 B2 | 3/2012 | Deem et al. | |
| 8,574,184 B2 * | 11/2013 | Errico | A61F 2/04 |
| | | | 604/8 |
| 10,543,008 B2 | 1/2020 | Vakharia | A61B 17/320092 |
| 2002/0078967 A1 * | 6/2002 | Sixto, Jr. | A61B 1/00073 |
| | | | 128/898 |
| 2005/0203547 A1 * | 9/2005 | Weller | A61B 17/072 |
| | | | 606/139 |
| 2005/0251160 A1 * | 11/2005 | Saadat | A61B 17/0401 |
| | | | 606/153 |
| 2008/0015567 A1 * | 1/2008 | Kimura | A61B 18/1442 |
| | | | 606/49 |
| 2008/0029574 A1 * | 2/2008 | Shelton | A61B 17/07207 |
| | | | 227/175.2 |
| 2009/0062791 A1 * | 3/2009 | Lee | A61B 18/1402 |
| | | | 606/45 |
| 2013/0018411 A1 * | 1/2013 | Collings | A61B 18/1442 |
| | | | 606/205 |
| 2013/0060250 A1 * | 3/2013 | Twomey | A61B 18/1447 |
| | | | 606/52 |
| 2013/0131651 A1 * | 5/2013 | Strobl | A61B 17/29 |
| | | | 606/1 |
| 2013/0178877 A1 * | 7/2013 | Bender | A61F 5/0086 |
| | | | 606/153 |
| 2013/0218198 A1 * | 8/2013 | Larson | A61B 18/1445 |
| | | | 606/206 |
| 2013/0304059 A1 * | 11/2013 | Allen, IV | A61B 17/285 |
| | | | 606/41 |
| 2014/0100600 A1 * | 4/2014 | Kendrick | A61B 17/320092 |
| | | | 606/205 |
| 2014/0114121 A1 | 4/2014 | Trivedi | |
| 2014/0249528 A1 * | 9/2014 | Hixson | A61B 18/1445 |
| | | | 606/51 |
| 2015/0133740 A1 | 5/2015 | Dierking et al. | |

OTHER PUBLICATIONS

Arthur Schmidt et al., "Endoscopic full-thickness resection: Current status," World Journal of Gastroenterology, Aug. 21, 2015 (14 pages).

* cited by examiner

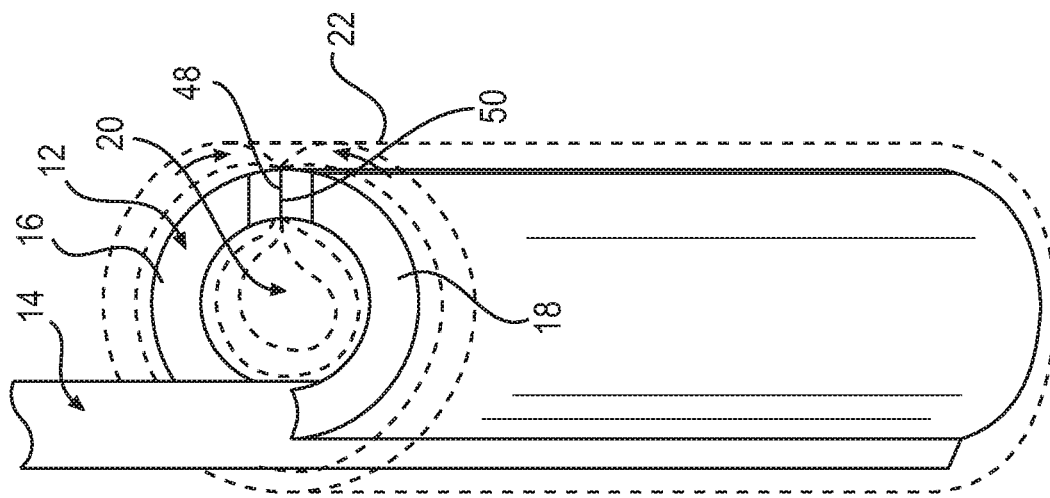
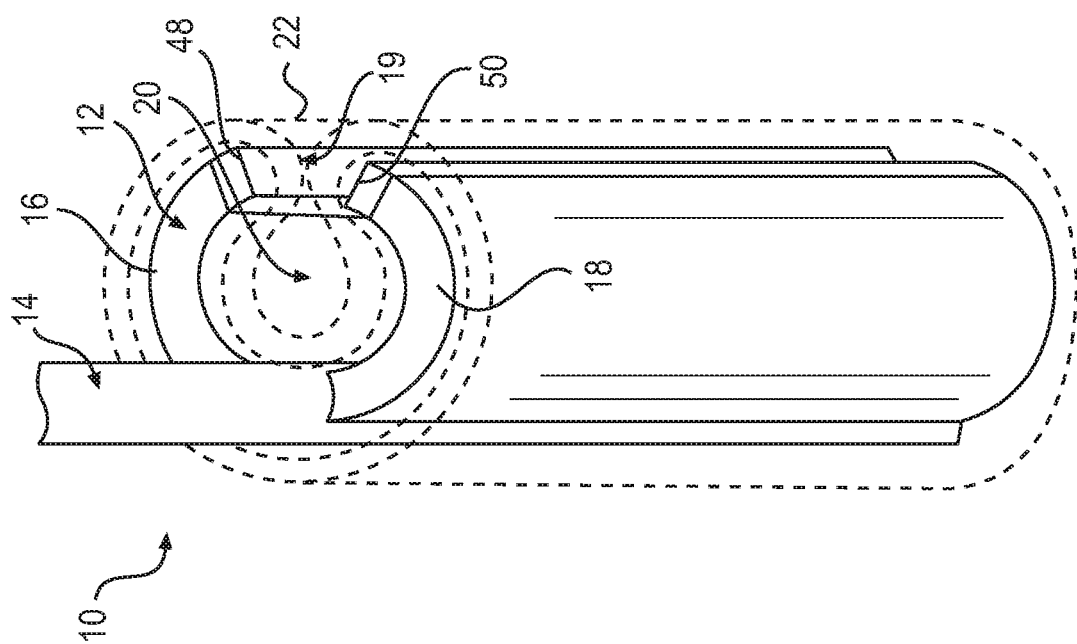

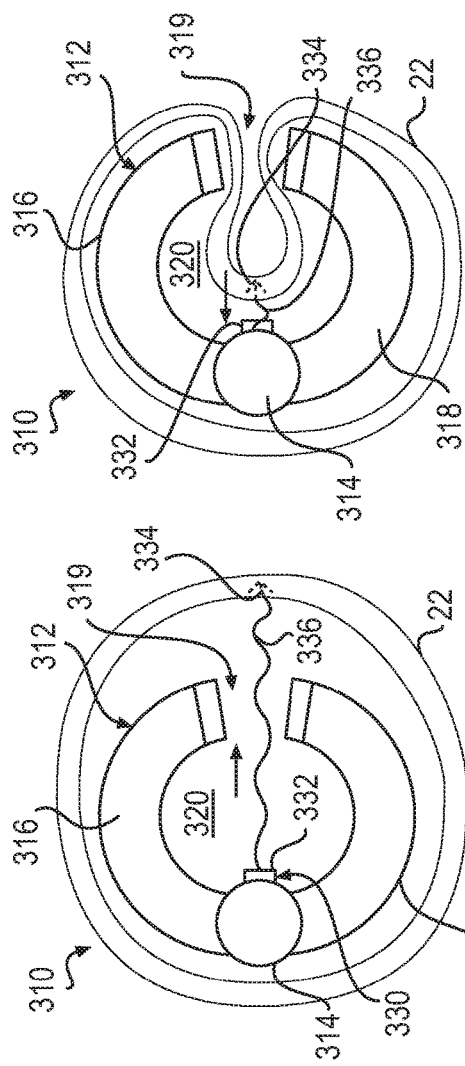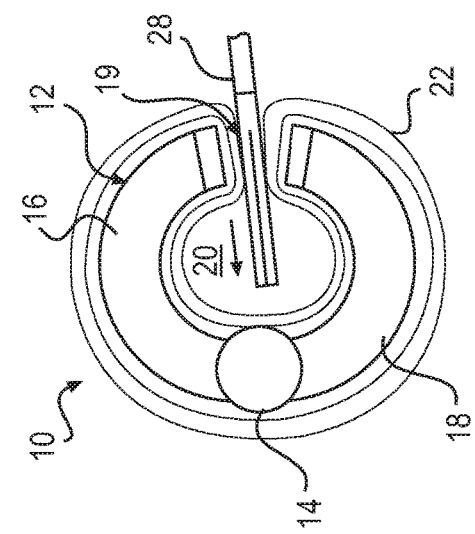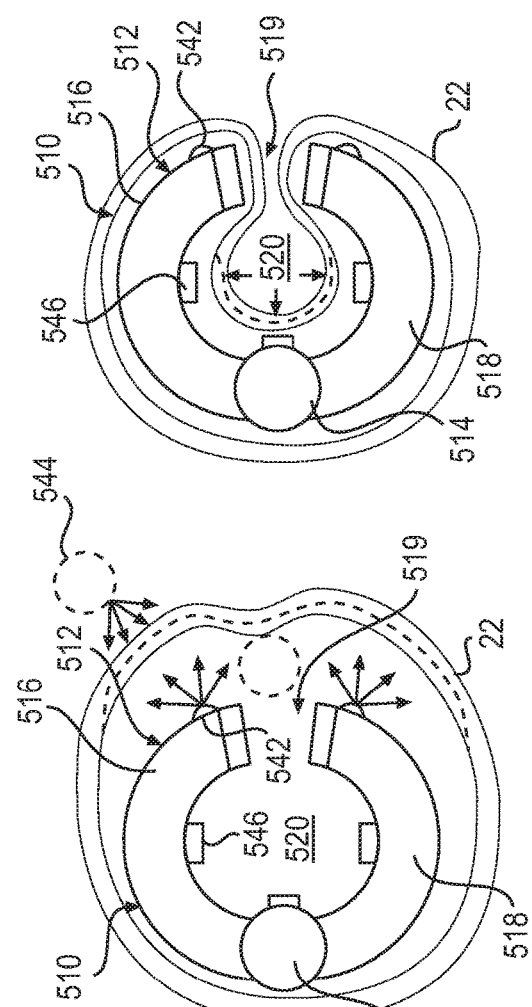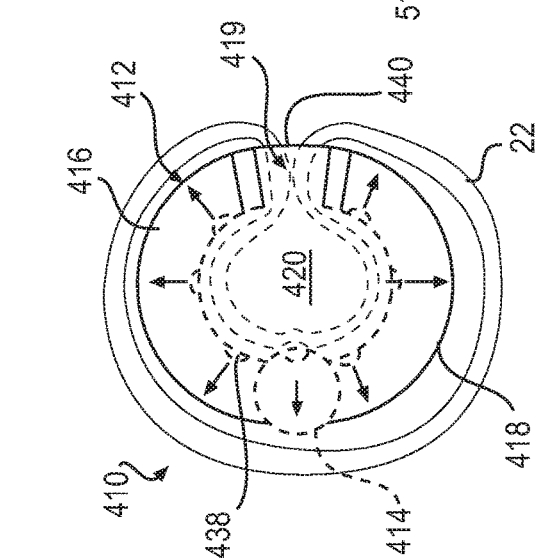

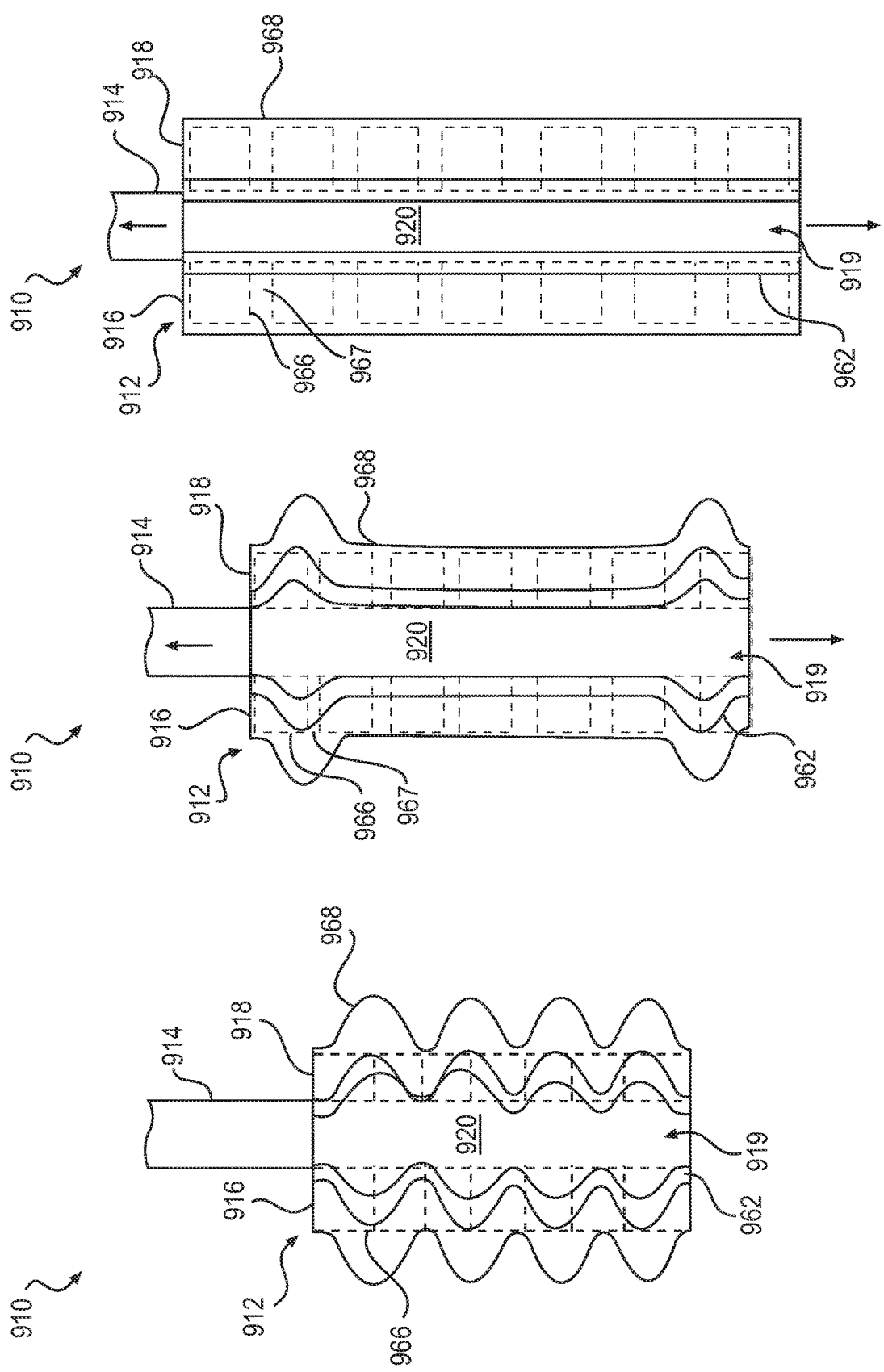

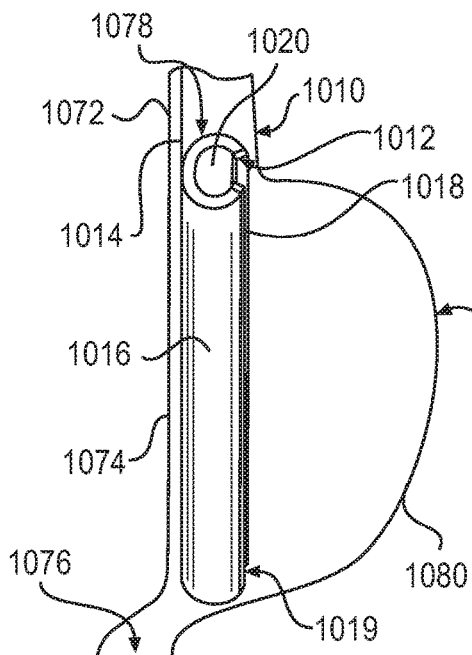
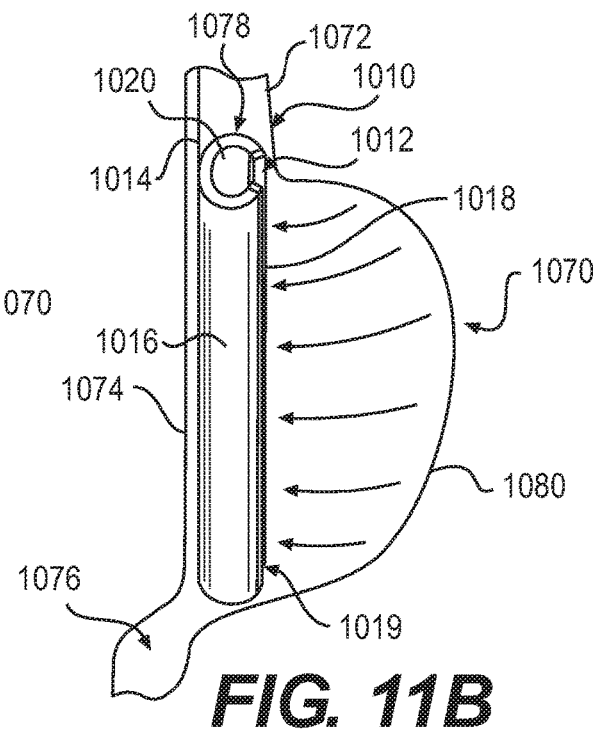
FIG. 11A  FIG. 11B
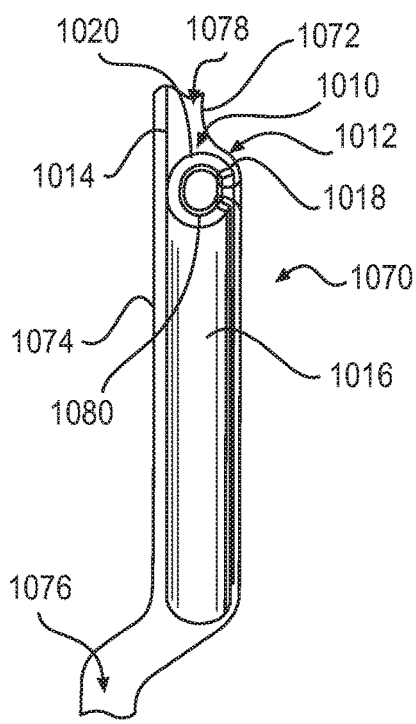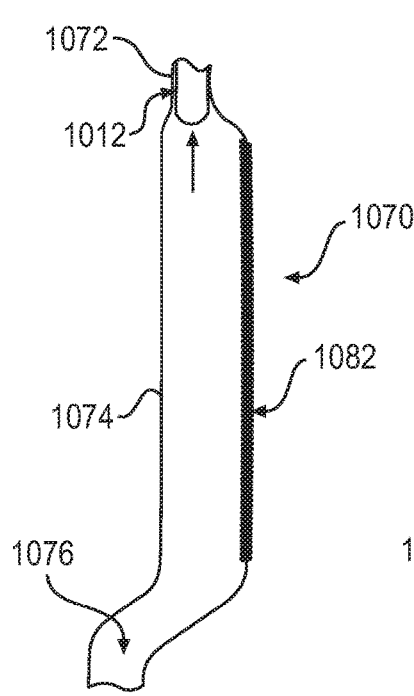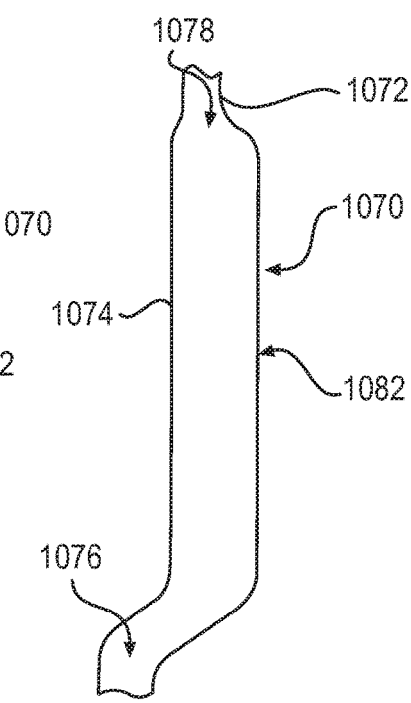
FIG. 11C  FIG. 11D  FIG. 11E

DEVICES AND RELATED METHODS FOR GASTRECTOMIES

CROSS-REFERENCE TO RELATED APPLICATIONS

This application claims the benefit of priority of U.S. Provisional Application No. 62/343,502, filed on May 31, 2016, which is incorporated herein by reference in its entirety.

TECHNICAL FIELD

Various aspects of the present disclosure relate generally to devices and related methods for gastrectomies. More specifically, the present disclosure relates to surgical devices and related methods for sleeve gastrectomies.

BACKGROUND

A gastrectomy is a procedure which may involve surgical removal of a part of a subject's stomach. One type of gastrectomy, a sleeve gastrectomy, is a procedure that may be performed on a subject to facilitate weight loss. In a sleeve gastrectomy, a portion of the subject's stomach along the greater curvature of the stomach may be removed, leaving a sleeve-like structure ("gastric sleeve") remaining. Conventionally, a sleeve gastrectomy may be performed laparoscopically, and may entail cutting the subject's stomach, and then stapling the subject's stomach to form the gastric sleeve. After undergoing such a procedure, the subject may be at risk of developing a post-surgical leak and associated fistulae at or near the location where the stomach was cut and/or stapled. Such leaks may complicate the subject's recovery from the procedure, and may be costly to treat. Thus, there remains a need for devices and related methods for gastrectomies, including sleeve gastrectomies, with improved capabilities and outcomes.

SUMMARY

Aspects of the disclosure relate to, among other things, devices and related methods for gastrectomies. Each of the aspects disclosed herein may include one or more of the features described in connection with any of the other disclosed aspects.

In one aspect of the present disclosure, an apparatus for treating tissue may include an elongate tube. The elongate tube may include a slot extending longitudinally along a first side of the elongate tube, a first elongate jaw member on a first side of the slot, and a second elongate jaw member on a second side of the slot. The apparatus may also include a shaft coupled to the elongate tube along a second side of the elongate tube. The first elongate jaw member may be movably coupled to the shaft, such that the first elongate jaw member may be movable toward the second elongate jaw member to converge tissue walls within the slot and cut the tissue walls within the slot.

Aspects of the apparatus may include one or more of the features below. The first elongate jaw member may include a first engaging surface defining the first side of the slot, and the second elongate jaw member may include a second engaging surface defining the second side of the slot. The apparatus may include a first strip coupled to the first elongate jaw member, the first strip including a first engaging surface defining the first side of the slot. The apparatus may include a second strip coupled to the second elongate jaw member, the second strip including a second engaging surface defining the second side of the slot. The first strip may be detachable from the first elongate jaw member. The second strip may be detachable from the second elongate jaw member. The first strip may include a protrusion protruding from the first engaging surface. The second strip may include a recess shaped and sized to receive the protrusion. The protrusion and the recess may form at least one of a snap-fit connection and a press seal connection. A length of the protrusion may be equal to a length of the first strip. A length of the recess may be equal to a length of the second strip. The length of the first strip may be equal to a length of the first elongate jaw member. The length of the second strip may be equal to a length of the second elongate jaw member. The elongate tube may be movable between an extended configuration, in which the elongate tube has a first length, and a contracted configuration, in which the elongate tube has a second length, the second length being shorter than the first length. The elongate tube may be deflectable from a straight configuration to a curved configuration. At least one of the first elongate jaw member and the second elongate jaw member may include an electrode. The apparatus may include at least one grasping assembly, wherein the grasping assembly includes a base, a grasping element, and a strand extending between the base and the grasping element, and the grasping element may be configured for deployment from the base through the slot. The apparatus may include at least one of a suction orifice and a magnet on an interior surface of the elongate tube. The first elongate jaw member may include a plurality of support members, and a sleeve supported by the plurality of support members.

In another aspect of the present disclosure, an apparatus for treating tissue may include a tubular member. The tubular member may include an opening extending longitudinally along a first side of the elongate tubular member. The tubular member also may include a first side portion having a detachable first engaging surface, wherein the detachable first engaging surface extends along a first side of the opening. The tubular member also may include a second side portion having a detachable second engaging surface, wherein the detachable second engaging surface extends along a second side of the opening. The apparatus also may include a shaft coupled to the elongate tubular member at a second side of the elongate member. The first side portion may be movably coupled to the shaft, such that the first side portion is movable toward the second side portion to move the detachable first engaging surface toward the detachable second engaging surface to converge tissue walls, and cut the tissue walls. One of the detachable first engaging surface and the detachable second engaging surface may include a protrusion, and the other of the detachable first engaging surface and the detachable second engaging surface may include a recess complementary to the protrusion.

Aspects of the apparatus may include one or more of the features below. The detachable first engaging surface may be part of a first strip that is removably attached to a surface of the first side portion, and the detachable second engaging surface may be part of a second strip that is removably attached to a surface of the second side portion. The first strip may be ferromagnetic, and the second strip may include a material that is magnetically attracted by the first strip.

In yet another aspect of the present disclosure, a method for treating tissue may include positioning an elongate tubular member adjacent tissue. The method also may include bringing a portion of the tissue through an opening extending longitudinally along a side of the elongate tubular member, to position two walls of the tissue between (a) a first side portion of the elongate tubular member having a first engaging surface, wherein the first engaging surface extends along a first side of the opening, and (b) a second side portion of the elongate tubular member having a second engaging surface, wherein the second engaging surface extends along a second side of the opening. The method also may include moving the first side portion toward the second side portion to move the first engaging surface toward the second engaging surface to converge the tissue walls toward one another and cut the tissue walls. Optionally, the method may include sealing the cut tissue walls via interlocking of the first engaging surface and the second engaging surface.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 1A and 1B are perspective views of a clamp of an endoscopic surgical device in open and closed configurations, in accordance with aspects of the present disclosure.

FIG. 4 is a top view of the clamp of FIGS. 1A and 1B, and an instrument for guiding material into the clamp, in accordance with aspects of the present disclosure.

FIGS. 5A and 5B are top views of a clamp of another endoscopic surgical device, with a grasping assembly for guiding material into the clamp, in accordance with aspects of the present disclosure.

FIG. 6 is a top view of a clamp of another endoscopic surgical device, with vacuum orifices for guiding material into the clamp, in accordance with aspects of the present disclosure.

FIGS. 7A and 7B are top views of a clamp of yet another endoscopic surgical device, with nozzles and magnets for guiding material into the clamp, in accordance with aspects of the present disclosure.

FIGS. 10A-10C are side views of a clamp of yet another endoscopic surgical device, with features for adjusting the length of the clamp, in accordance with aspects of the present disclosure.

FIGS. 11A-11E are schematic diagrams illustrating a performance of a sleeve gastrectomy procedure, in accordance with aspects of the present disclosure.

DETAILED DESCRIPTION

Figure 2A:
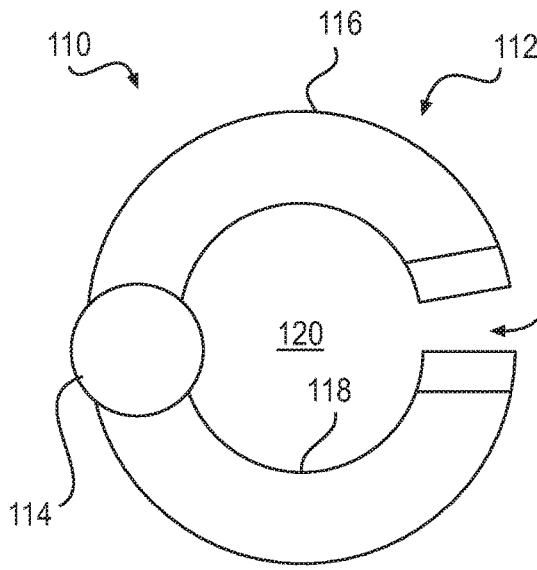
FIGS. 2A and 2B are top views of a clamp of another endoscopic surgical device in open and closed configurations, in accordance with aspects of the present disclosure.

The present disclosure is drawn to devices and related methods for gastrectomies. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient.

FIGS. 1A and 1B show a distal end portion of an endoscopic surgical device 10. Surgical device 10 may include a clamp 12, a shaft 14, and a handle (not shown). The handle may form a proximal end portion of surgical device 10. Shaft 14 may extend from the handle to clamp 12. Clamp 12 may be coupled to a distal end portion of shaft 14. The handle may include one or more control members (not shown) configured to control operation of shaft 14 and/or clamp 12. For example, the handle may include one or more of a rotatable steering knob, trigger, button, slider, or other suitable actuator, which may be coupled to one or more of a wire, drive shaft, gear assembly, motor, pneumatic line, or other suitable force transmission element, to control operations of clamp 12 and/or shaft 14 in the ways that are described below.

Clamp Features

FIG. 1A shows clamp 12 in an open configuration. Clamp 12 may include a first side portion or jaw member 16 and a second side portion or jaw member 18. An opening 19 may be defined between free ends of first and second jaw members 16, 18 when clamp 12 is in the open configuration. Opening 19 may define a longitudinally-extending slot. Opening 19 may open into a central passage 20 through clamp 12. Material 22, which may include a tissue wall in a subject's body, such as stomach wall tissue, is shown in dashed line around clamp 12. Material 22 may extend about outer surfaces of first and second jaw members 16, 18. A portion of material 22, which may be inverted, may be guided into central passage 20 via opening 19. FIG. 1B shows clamp 12 in a closed configuration. The free ends of first and second jaw members 16, 18 may be moved toward each other (thus closing opening 19) to move clamp 12 to the closed configuration. The free ends of first and second jaw members 16, 18 may come into direct contact. Alternatively, the free ends of first and second jaw members 16, 18 may remain separate due, for example, to material 22 being trapped between the free ends.

At least one of first and second jaw members 16, 18 may be movably coupled to shaft 14 to facilitate movement of clamp 12 between the open configuration and the closed configuration. FIGS. 1A and 1B show an example of clamp 12 where first and second jaw members 16, 18 are both movably coupled to shaft 14 (via, for example, a hinge connection), such that first and second jaw members 16, 18 pivot away from each other to move clamp 12 to its open configuration, and toward each other to move clamp 12 to its closed configuration.

Figure 2B:
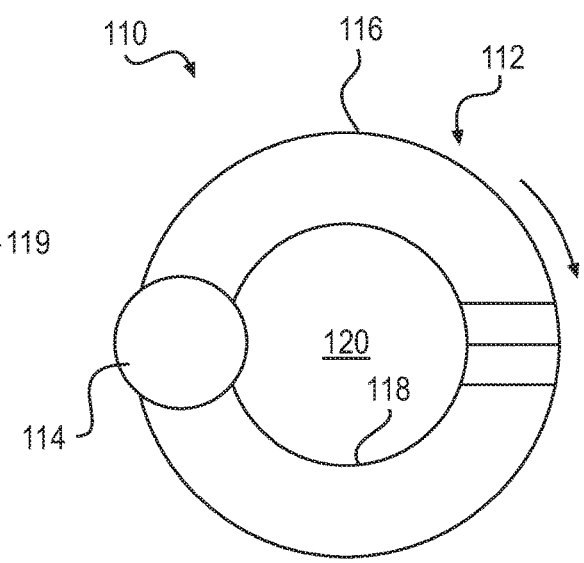

FIGS. 2A and 2B show an endoscopic surgical device 110, shaft 114, clamp 112, first jaw member 116, second jaw member 118, opening 119, and central passage 120, similar to those shown in FIGS. 1A and 1B. Surgical device 110 differs in that first jaw member 116 may be movably coupled to shaft 114, while second jaw member 118 may be fixedly coupled to shaft 114. In this example, first jaw member 116 may pivot towards and away from second jaw member 118 while second jaw member 118 remains static, to move clamp 112 into the closed and open configurations, respectively.

Figure 3A:
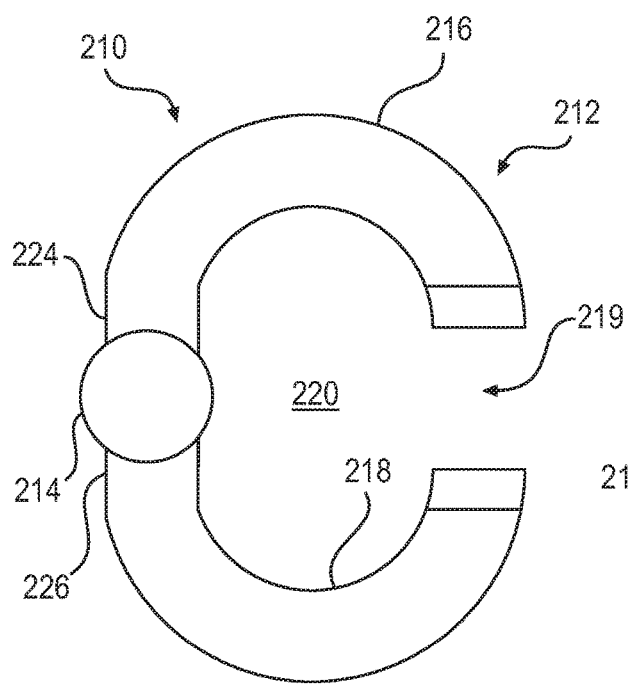
FIGS. 3A and 3B are top views of a clamp of yet another endoscopic surgical device in open and closed configurations, in accordance with aspects of the present disclosure.
Figure 3B:
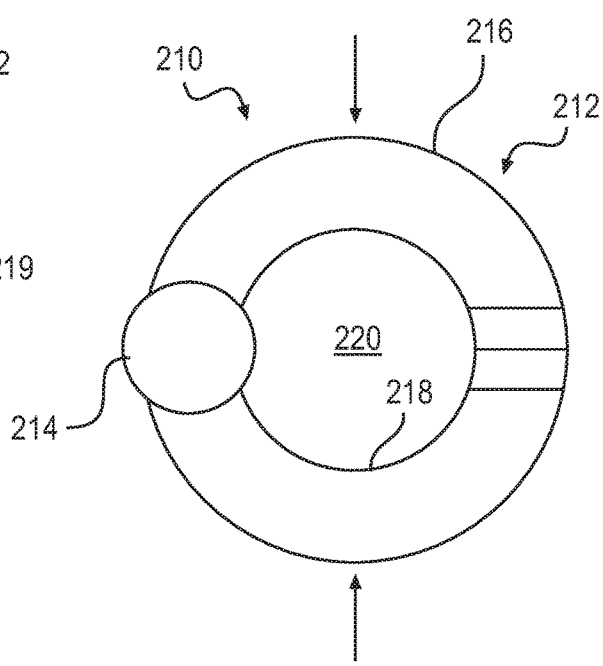

FIGS. 3A and 3B show an endoscopic surgical device 210, shaft 214, clamp 212, first jaw member 216, second jaw member 218, opening 219, and central passage 220, similar to those shown in FIGS. 1A and 1B. Surgical device 210 differs in that first and second jaw members 216, 218 may be movably coupled to shaft 214 (via, for example, a linear drive connection) such that first and second jaw members 216, 218 may shift away from each other in a translational manner to move surgical device 210 into the open configuration, and first and second jaw members 216, 218 may shift toward each other to move surgical device 210 into the closed configuration (as shown by arrows in FIG. 3B). It is contemplated that first and second jaw members 216, 218 may include linear portions 224, 226 where they meet shaft 214 to facilitate the translational opening and closing movements. Alternatively, first jaw member 216 may be movably coupled to shaft 214 while second jaw member 218 may be fixedly coupled to shaft 214, similar to the arrangement shown in FIGS. 2A and 2B (but with translational movements instead of pivoting). It is also contemplated that one or more of clamps 12, 112, 212, and any other clamps described herein, may move between the open and closed configurations using a combination of pivoting and translational movements.

As noted above, the handle (not shown) and any of shafts 14, 114, 214, and any other shafts described herein, may include one or more control members (for example, a steering knob, trigger, button, slider, or other suitable actuator), and/or one or more force transmission elements (for example, a wire, drive shaft, gear assembly, pneumatic line, motor, or other suitable element), to cause movement of clamps 12, 112, 212, and/or any other clamps described herein, between their respective open and closed configurations. Additionally or alternatively, the free ends of the first and second jaw members of clamps 12, 112, 212, and/or any other clamps described herein, may be magnetized, with the free ends of each of the pairs having opposite polarity such that the free ends attract each other. In such an example, the open configuration may be attained by keeping the free ends far enough apart that the attractive force between them cannot draw them together, or by forcibly keeping the free ends apart via the one or more force transmission elements described above.

While clamps 12, 112, 212 are each tubular and have a C-shaped cross-sectional profile in FIGS. 1A, 1B, 2A, 2B, 3A, and 3B, it should be understood that other cross-sectional profiles may be used. For example, one or more of clamps 12, 112, 212 may have an elliptical cross-sectional profile, a D-shaped cross-sectional profile, a polygonal cross-sectional profile, or an irregularly-shaped cross sectional profile. The particular type of cross-sectional profile selected may depend on factors including, for example, the environment of use, the amount of material 22 to be clamped, cut, and sealed, and/or the type of material 22 to be acted on, among other factors.

Internalizing Material

The insertion of material 22 into clamps 12, 112, 212, and/or any other clamps described herein, may be carried out in any suitable manner. A few examples of ways in which the insertion of material 22 may be carried out will now be described with reference to FIGS. 4, 5A, 5B, 6, 7A, and 7B.

It should be understood that each of the ways shown in FIGS. 4, 5A, 5B, 6, 7A, and 7B may be used on its own, or used in combination with one or more of the others.

FIG. 4 shows surgical device 10 with its clamp 12 in the open configuration, and with an instrument 28 guiding material 22 into central passage 20 via opening 19. Instrument 28 may include, for example, a forceps. A user may open the forceps and close it on material 22 to grasp material 22. The user may maneuver the forceps to push and pull the grasped material 22. Instrument 28 may be introduced into the subject laparoscopically, such that it may engage an outer surface of material 22 to stuff material 22 through opening 19 and into central passage 20, as shown in FIG. 4. Alternatively, instrument 28 may be introduced into the subject with surgical device 10, such that it may be at least initially positioned within central passage 20, may move out of central passage 20 via opening 19 to engage an inner surface of material 22, and may pull material 22 into central passage 20 through opening 19. It should be understood that material 22 in central passage 20 may, for example, have a cross-sectional shape of a single loop, a plurality of lobes, and/or a spiral roll, depending on how much material 22 is contained in central passage 20.

FIGS. 5A and 5B show a surgical device 310, shaft 314, clamp 312, first jaw member 316, second jaw member 318, opening 319, and central passage 320 similar to those shown in FIGS. 1A and 1B. In FIG. 5A, material 22 is shown prior to being inserted into central passage 320 and extending around the outside of clamp 312. Surgical device 310 may include a grasping assembly 330 for guiding material 22 into clamp 312. Grasping assembly 330 may include a base 332, a grasping element 334 (for example, a barb), and a strand 336 (for example, a string, filament, cable, or wire) connecting base 332 to grasping element 334. Base 332 may be mounted on shaft 314. Initially, grasping element 334 may be coupled to base 332, with grasping element 334 facing away from base 332 and toward opening 319. Strand 336 may be stored in shaft 314 and/or base 332, or may hang freely from base 332. Grasping element 334 may be propelled from base 332 as a projectile. The propulsion may be provided by, for example, pressurized gas in a pneumatic line (not shown) extending through shaft 14 and in communication with base 332. Once fired, grasping element 334 may sail across central passage 320, through opening 319, and into material 22. Grasping element 334 may at least partially penetrate and embed into material 22, thereby coupling to material 22. A user may pull a proximal end of strand 336, or may actuate a mechanism (similar to a winch) in base 332, shaft 314, or the handle, to pull strand 336. The pulling may draw material 22 through opening 319 and into central passage 320, as shown in FIG. 5B. Material 22 may be pulled until adjacent to, or in contact with, base 332. It should be understood that a plurality of grasping assemblies may be provided on shaft 314. The grasping assemblies may be, for example, aligned longitudinally along the surface of shaft 314 that faces opening 319. The plurality of grasping assemblies may be fired simultaneously or at different times. Each of the strands of the grasping assemblies may be pulled at the same time or at different times. For example, the distalmost strand may be pulled first, followed by the strand proximal to the distalmost strand, after a delay. This pattern may be repeated going proximally to the proximalmost strand.

Additionally or alternatively, strand(s) 336 and grasping element(s) 334 may be replaced by a relatively rigid cable or wire having a barbed or hooked tip. The cable/wire may be pushed to extend away from shaft 314, through opening 319, and into material 22. After engaging material 22 with the barbed/hooked tip, the cable/wire may be pulled back toward shaft 314 to move material 22 through opening 319 into central passage 320.

FIG. 6 shows a surgical device 410, shaft 414, clamp 412, first jaw member 416, second jaw member 418, opening 419, and central passage 420 similar to those shown in FIGS. 1A and 1B. One or more of first and second jaw members 416, 418 may include one or more suction orifices 438. Each suction orifice 438 may be coupled to one or more suction lumens (not shown) in shaft 414, first jaw member 416, and/or second jaw member 418. The one or more suction lumens may be coupled to a vacuum source (not shown). Clamp 412 may include a cap 440 covering a proximal end of central passage 420. Cap 440 may include, for example, a flexible membrane that may be capable of covering central passage 420 when clamp 412 is in the open configuration, without hindering movement of clamp 412 into the closed configuration. Clamp 412 also may include a similar cap (not shown) covering a distal end of central passage 420. The caps may help ensure that the suction force generated in central passage 420 by one or more suction orifices 438 may be concentrated at opening 419 to facilitate the drawing in of material 22 through opening 419 and into central passage 420. It is contemplated that suction orifices 438 may be spaced circumferentially, as shown in FIG. 6, and/or longitudinally. Additionally or alternatively, suction orifices 438 may be activated simultaneously, or in sequence. For example, a distalmost suction orifice may be activated first, followed by the suction orifice proximal to the distalmost suction orifice, after a delay. This pattern may be repeated going proximally to the proximalmost suction orifice.

FIGS. 7A and 7B show a surgical device 510, shaft 514, clamp 512, first jaw member 516, second jaw member 518, opening 519, and central passage 520, similar to those shown in FIGS. 1A and 1B. One or more of shaft 514, first jaw member 516, and second jaw member 518 may include one or more nozzles 542. Each nozzle 542 may be coupled to one or more fluid lumens (not shown) in shaft 514, first jaw member 516, and/or second jaw member 518. The one or more fluid lumens may be coupled to a fluid source (not shown). The fluid source may include, for example, a supply of one or more of the following: a magnetic paint (for example, a fluid containing magnetic particles or beads); a polymer solution, sol-gel, particulate suspension, or melt, with magnetic particles or beads therein, that may exit nozzle(s) 542 in the form a liquid jet, and dry or cure in flight to form magnetic fiber(s); and/or any other magnetic material that can be sprayed onto a surface. One or more of the fluids may be sprayed onto material 22 via nozzle(s) 542, as shown in FIG. 7A. Additionally or alternatively, fluid(s) may be sprayed onto material 22 by one or more instruments 544 separate from surgical device 510. The sprayed fluid(s) may stick to material 22, coat material 22, partially or fully solidify on material 22, and/or may be absorbed into material 22. The outer surface and/or the inner surface of material 22 may be sprayed. Once sprayed, material 22 may be drawn into central passage 520 by magnetic attraction between the applied fluid(s) and one or more magnets 546 on one or more of shaft 514, first jaw member 516, and second jaw member 518, as shown in FIG. 7B. It is contemplated that nozzles 542 may be spaced circumferentially, as shown in FIGS. 7A, 7B, and/or longitudinally. Additionally or alternatively, nozzles 542 may be activated simultaneously, or in sequence from distal to proximal. It is also contemplated that magnets 546 may be spaced circumferentially and/or longitudinally. Additionally or alternatively, magnets 546 may be activated simultaneously, or in sequence from distal to proximal.

Clamping, Cutting, and Sealing

Each of the above-described clamps may clamp and cut material 22 as the clamp moves toward the closed configuration. It should be understood that the following description of the manner in which clamping and cutting is performed with clamp 12 is applicable to clamps 112, 212, 312, 412, and 512. As shown in FIG. 1A, material 22 may be positioned in central passage 20 and opening 19 in preparation for cutting to be performed. Clamp 12 may move toward the closed configuration to clamp and cut the portion of material 22 between a first engaging surface 48 of first jaw member 16 and a second engaging surface 50 of second jaw member 18. The length of the cut may be equal to the lengths of first and second engaging surfaces 48, 50. Alternatively, the length of the cut may be less than the lengths of first and second engaging surfaces 48, 50, if a length of material 22 in opening 19 is less than the lengths of first and second engaging surfaces 48, 50.

Figure 8A:
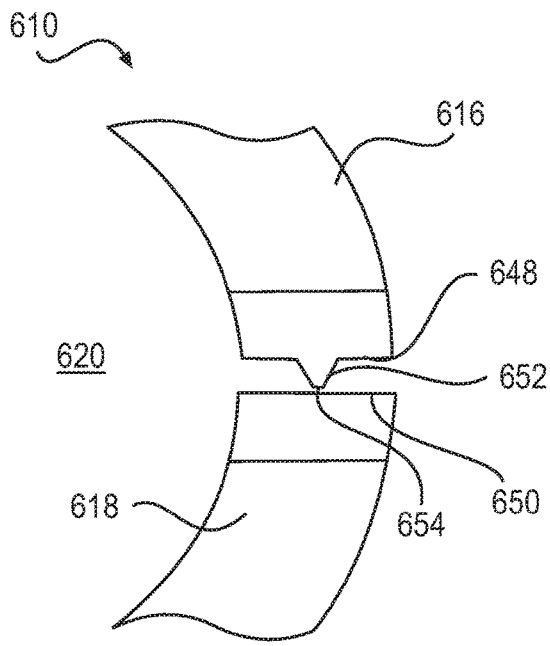
FIG. 8A is a partial top view of a clamp of yet another endoscopic surgical device, with a cutting element for cutting and/or sealing material, in accordance with aspects of the present disclosure.
Figure 8B:
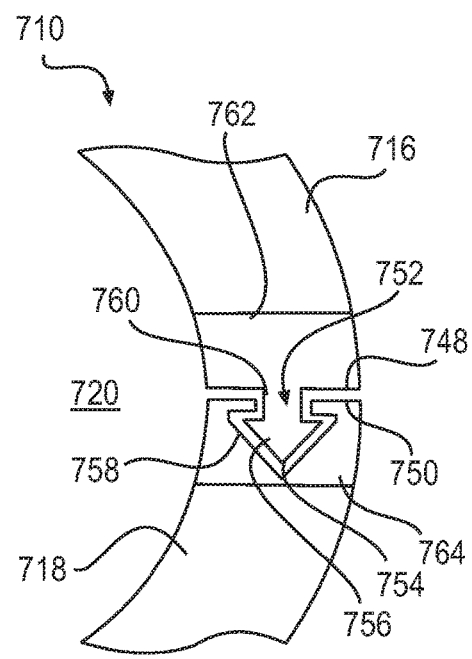
FIG. 8B is a partial top view of a clamp of yet another endoscopic surgical device, with another cutting element for cutting and/or sealing material, in accordance with aspects of the present disclosure.

FIGS. 8A and 8B show examples of surgical devices with features for facilitating clamping and cutting of material 22. For example, FIG. 8A shows a surgical device 610 including a first jaw member 616 having a first engaging surface 648 with a cutting element 652 in the form of a protrusion. Cutting element 652 may extend the full length of first engaging surface 648. Cutting element 652 may have a sharp edge 654. As first and second engaging surfaces 648, 650 are brought together, cutting element 652, beginning with sharp edge 654, may press (clamp) material 22 against second engaging surface 650, and vice-versa. Continued movement may cause sharp edge 654 to cut material 22. Sharp edge 654 may eventually come into direct contact with second engaging surface 650, after fully cutting through material 22. The cut portion of material 22, which may include the portion of material 22 extending from a radially-inward facing side of cutting element 652 into central passage 620, may be removed from the subject. It should be understood that cutting element 652 may have any other suitable cross-sectional shape including, for example, a semi-circular, polygonal, and/or irregular cross-sectional shape. It is contemplated that second engaging surface 650 may include a cutting element (not shown) similar to cutting element 652. The cutting element of second engaging surface 650 may contact cutting element 652 to facilitate cutting in a manner similar to scissor blades. Additionally or alternatively, second engaging surface 650 may include a recess (not shown) for receiving at least a portion of cutting element 652, thereby reducing or eliminating any gap between first engaging surface 648 and second engaging surface 650. Additionally or alternatively, cutting elements may be positioned at any location along first engaging surface 648 and second engaging surface 650, respectively, not just located along their centers. Additionally or alternatively, a plurality of cutting elements may be provided on first engaging surface 648 and/or second engaging surface 650. Alternatively, neither of first and second engaging surfaces 648, 650 may have any cutting elements, and cutting may be performed by first and second jaw members 616, 618 by forcing first and second engaging surfaces 648, 650 together with sufficient pressure to squeeze material 22 out from between them. Eventually, material 22 may separate. Aspects of first and second jaw members 616, 618 may be used with any of first and second jaw members 16, 18, first and second jaw members 116, 118, first and second jaw members 216, 218, first and second jaw members 316, 318, first and second jaw members 416, 418, first and second jaw members 516, 518, and/or any other jaw members described herein.

FIG. 8B shows a surgical device 710 including a first jaw member 716 having a first engaging surface 748 with a cutting element 752 in the form of a protrusion. Cutting element 752 may extend the length of first engaging surface 748. Cutting element 752 may have a stem 760, and an enlarged end portion 756 having one or more sharp edges 754. A second jaw member 718 may include a second engaging surface 750 having a recess 758 formed therein. Recess 758 may extend the length of second engaging surface 750. Recess 758 may have a shape complementary to that of cutting element 752. As first and second engaging surfaces 748, 750 are brought closer together, cutting element 752 may cut material 22 as cutting element 752 approaches and/or enters recess 758. Cutting element 752 may interlock with recess 758 (for example, via a snap-fit and/or press seal/press-seal/press-and-seal/ziplock/zipper engagement), forming a secure seal. It should be understood that cutting element 752 may have any other suitable cross-sectional shape including, for example, a hook, T, and/or any other suitable shape; and recess 758 may have any suitable complementary cross-sectional shape. Additionally or alternatively, cutting element 752 and recess 758 may be positioned at any location along first and second engaging surfaces 748, 750, respectively, not just located along their centers. Additionally or alternatively, a plurality of cutting elements and recesses may be provided. Aspects of first and second jaw members 716, 718 may be used with any of first and second jaw members 16, 18, first and second jaw members 116, 118, first and second jaw members 216, 218, first and second jaw members 316, 318, first and second jaw members 416, 418, first and second jaw members 516, 518, and/or any other jaw members described herein. Additionally or alternatively, cutting element 752 and recess 758 may be engaged in stages, beginning at their distal ends and progressing proximally to finish at their proximal ends.

One or more of first and second jaw members 716, 718 may include a magnet, or may otherwise be magnetic. For example, one of first and second engaging surfaces 748, 750 may be part of a magnet (such as a ferromagnetic permanent magnet), and the other of first and second engaging surfaces 748, 750 may be a material attracted by the magnet. It is also contemplated that both of first and second engaging surfaces 748, 750 may be magnets with opposite polarities, and thus, they may be attracted to each other. The magnetic attraction may facilitate cutting of material 22 by forcing first and second engaging surfaces 748, 750 together. Additionally or alternatively, one of first and second engaging surfaces 748, 750 may be an electrode (for example, a high-frequency electrode). It is also contemplated that both of first and second engaging surfaces 748, 750 may be electrodes. When energized, the electrode(s) may heat material 22 by directing an electrical current into material 22. Material 22 affected by the electrical current may, for example, vaporize, forming a cut in material 22. By using a different type and/or amount of electrical energy or current, material 22 at the cut may be cauterized to help seal the cut. Additionally or alternatively, one of first and second engaging surfaces 748, 750 may vibrate at a high (for example, ultrasonic) frequency. It is also contemplated that both of first and second engaging surfaces 748, 750 may vibrate at a high frequency. The vibration may heat material 22 via friction, causing portions of material 22 exposed to the heat to break down, thereby forming a cut in material 22. By using a different type and/or amount of ultrasonic energy, material 22 at the cut may be coagulated to help seal the cut. While described with respect to first and second jaw members 716, 718, it should be understood that one or more of the above-described features for facilitating cutting via magnetic attraction, electrosurgery, and/or ultrasound may be used with any of first and second jaw members 16, 18, first and second jaw members 116, 118, first and second jaw members 216, 218, first and second jaw members 316, 318, first and second jaw members 416, 418, first and second jaw members 516, 518, first and second jaw members 616, 618, and/or any other jaw members described herein.

First and second jaw members 16, 18, first and second jaw members 116, 118, first and second jaw members 216, 218, first and second jaw members 316, 318, first and second jaw members 416, 418, first and second jaw members 516, 518, first and second jaw members 616, 618, first and second jaw members 716, 718, and/or any other jaw members described herein, may have a strip on its free end. The strip may include the engaging surface for cutting material 22. FIG. 8B, for example, shows first jaw member 716 including a first strip 762 and second jaw member 718 including a second strip 764. First strip 762 and/or second strip 764 may be removably coupled to its corresponding jaw member. The removable coupling allows first strip 762 and/or second strip 764 to be replaced with other strips. The other strips may, for example, have different properties. For example, the other strips may have different cutting elements and/or recesses. Additionally or alternatively, the other strips may have different capabilities when it comes to facilitating cutting via magnetic attraction, electrosurgery, and/or ultrasound. It is also contemplated that the removable coupling allows first strip 762 and second strip 764 to remain engaged to each other, and to material 22 (for example, at or near the cut in material 22), to maintain a secure seal at the cut and prevent leakage. The removable coupling also may allow magnetically attracted strips to remain engaged to each other, and to material 22 at or near the cut in material 22, for similar purposes. Any suitable mechanism may be provided to removably couple first and second strips 762, 764, including, for example, providing weakened regions that can be torn to detach the strips, securing the strips to their jaw members by releasable connections (such as by snap-fit), and/or utilizing releasable latches between the strips and their jaw members that can be released via an actuator on the handle. It is further contemplated that strips may engage material 22 and each other via one or more staples along their lengths.

The strips may be loaded with one or more substances that undergo a change in properties when inside a subject's body. For example, the strips may be coated with a sealant that, when in a low pH environment outside of the subject, does not release from the strips. Once in a high pH environment inside of the subject, the sealant may be released by the strips to safeguard against leaking at or near the cut. Additionally or alternatively, the strips may be loaded with a healing/therapeutic agent(s), such as CD34 antigen or stem cells (or stem cell factors), to accelerate healing of material 22 at or near the cut. Additionally or alternatively, the strips may be made of biodegradable material (including, but not limited to, polylactic acid (PLA), polyglycolic acid (PGA), copolymers of PLA and PGA, poly-L-lactide (PLLA), poly-D,L-lactide (PDLA), poly-capralactone (PCL), and combinations thereof) to allow degradation around the cut for aiding healing at or near the cut, surgical grade stainless steel, spring steel, conductive polymers, ceramic porcelain, glass-like material, and/or any other suitable material(s).

Adjustment of Length, Width, and/or Curvature

FIGS. 9A and 9B and 10A-10D show exemplary surgical devices with adjustment features. The adjustment features, used alone or in combination, may provide the surgical devices with the ability to adapt to fit a subject's anatomy. It should be understood that any of the adjustment features described below may be used in combination with features described with respect to any of surgical devices 10, 110, 210, 310, 410, 510, 610, 710, and other surgical devices described herein.

Figure 9A:
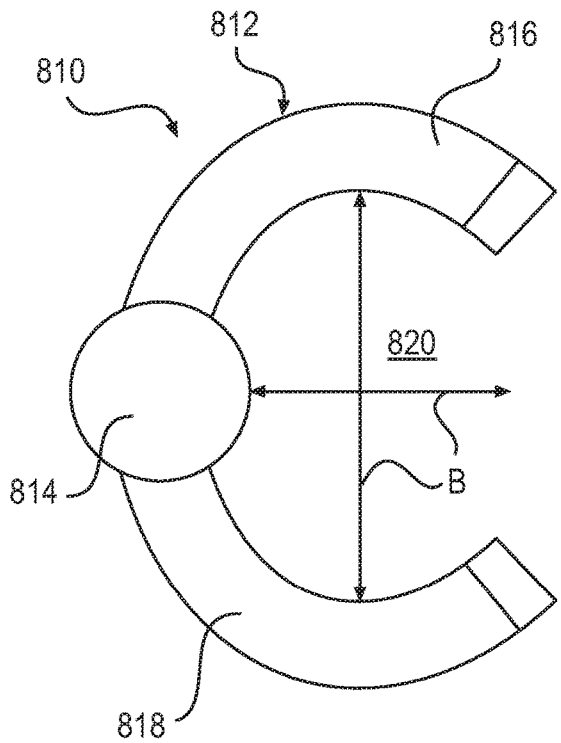
FIGS. 9A and 9B are top views of a clamp of yet another endoscopic surgical device, with features for adjusting the width of the clamp, in accordance with aspects of the present disclosure.
Figure 9B:
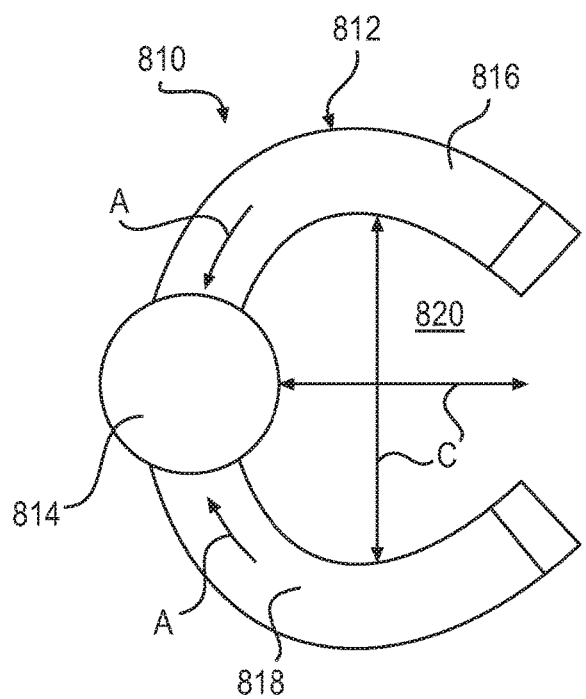

FIGS. 9A and 9B show an adjustable surgical device 810 including a clamp 812. Clamp 812 may include a first jaw member 816 movably coupled to a shaft 814, and an opposing second jaw member 818 movable coupled to shaft 814. FIG. 9A shows clamp 812 in a first open configuration. Clamp 812 may move from the first open configuration to a first closed configuration by, for example, pivoting at least one of first and second jaw members 816, 818 toward the other of first and second jaw members 816, 818. FIG. 9B shows clamp 812 in a second open configuration. Clamp 812 may be moved from the first open configuration to the second open configuration by retracting first and second jaw members 816, 818 into shaft 814, as shown by arrows A in FIG. 9B. Clamp 812 may move from the second open configuration to a second closed configuration by, for example, pivoting at least one of the shortened first and second jaw members 816, 818 toward the other of the shortened first and second jaw members 816, 818. First jaw member 816, second jaw member 818, shaft 814, and a central passage 820 of clamp 812 may have a larger cross-sectional area in the first open configuration (cross-sectional area represented by arrows B) than in the second open configuration (cross-sectional area represented by arrows C). Similarly, first jaw member 816, second jaw member 818, shaft 814, and a central passage 820 of clamp 812 may have a larger cross-sectional area in the first closed configuration than in the second closed configuration. The cross-sectional area defined by material 22, after cutting and removal of a portion of material 22, may be proportional to the cross-sectional area of clamp 812 in its closed configuration. As such, the cross-sectional area defined by material 22 may be smaller when clamp 812 clamps, cuts, and seals material 22 by moving from the second open configuration to the second closed configuration, than when clamp 812 clamps, cuts, and seals material 22 by moving from the first open configuration to the first closed configuration.

FIGS. 10A-10C show an adjustable surgical device 910 including a clamp 912 having an opening 919 and a central passage 920 for receiving material 22. Clamp 912 may be movably coupled to shaft 914 to not only move between an open configuration (FIGS. 10A-10C) and a closed configuration (not shown), but also to move between an extended configuration (FIG. 10C) and a contracted configuration (FIG. 10A).

For example, a first jaw member 916 may be movably coupled to a shaft 914 to pivot from the open configuration to the closed configuration (and vice-versa), and to slide longitudinally relative to shaft 914 from the contracted configuration to the extended configuration (and vice-versa). First jaw member 916 may include a plurality of support members 966 (shown by dashed lines) slidably coupled to shaft 914. Support members 966 may include, for example, curved rigid arms. Support members 966 may be polymeric, metallic, or made of any other suitable material.

Support members 966 may be covered by a flexible sleeve 968, and flexible sleeve 968 may be coupled to a similarly flexible strip 962. Flexible strip 962 may be similar to, for example, strip 762. In the contracted configuration of clamp 912, support members 966 may be positioned adjacent one another, for example, with a proximal surface of a support member directly contacting a distal surface of a proximally-adjacent support member, and/or a distal surface of the support member directly contacting a proximal surface of a distally-adjacent support member. Flexible sleeve 968 may be concertinaed and may include a plurality of bends or folds.

As clamp 912 moves from the contracted configuration toward the extended configuration, support members 966 may move away from each other, causing gaps 967 to form therebetween, and causing the size of those gaps 967 to increase. The movement of support members 966 may extend flexible sleeve 968, thereby reducing the size and/or number of bends or folds. FIG. 10B shows an example where support members 966 are moved in proximal and distal directions to extend clamp 912. It is also contemplated, however, that support members 966 may be moved in only the proximal direction, or only the distal direction, to extend clamp 912.

When clamp 912 reaches the fully extended configuration (FIG. 10C), flexible sleeve 968 may be fully extended, such that the bends or folds are no longer present. It should be understood that clamp 912 may be set (for example, selectively locked) at its extended configuration, contracted configuration, and any configuration therebetween, by the user. Shaft 914 may include a longitudinally-extending slot (not shown) to accommodate sliding of support members 966. Sliding of support members 966 may be caused by one or more actuators (not shown) within shaft 914 that may allow independent movement of support members 966. For example, the one or more actuators may include one or more telescoping rods, individually actuatable wires for pulling support members 966 along one or more tracks, and/or lost-motion connections between support members 966.

Second jaw member 918 may be similar to first jaw member 916. For example, second jaw member 918 may include support members similar to support member 966, a flexible sleeve similar to flexible sleeve 968, and a flexible strip similar to flexible strip 962. Alternatively, a single flexible sleeve may cover both first jaw member 916 and second jaw member 918.

Second jaw member 918 may be a mirror image of first jaw member 916 in the extended configuration, the contracted configuration, and positions therebetween. The length of material 22 inserted into clamp 912 may be equal to or less than the length of the extended portion of clamp 912. For example, the length of material 22 inserted into clamp 912, when clamp 912 is in the intermediate configuration shown in FIG. 10B, may be equal to or less than the extended central portion of clamp 912. On the other hand, the length of material 22 inserted into clamp 912, when clamp 912 is in the extended configuration shown in FIG. 10C, may be equal to or less than the full length of clamp 912. It is contemplated that clamp 912 may be moved into the closed configuration to engage material 22 from the open, intermediate configuration shown in FIG. 10B and/or from the open, extended configuration shown in FIG. 10C.

Figure 10D:
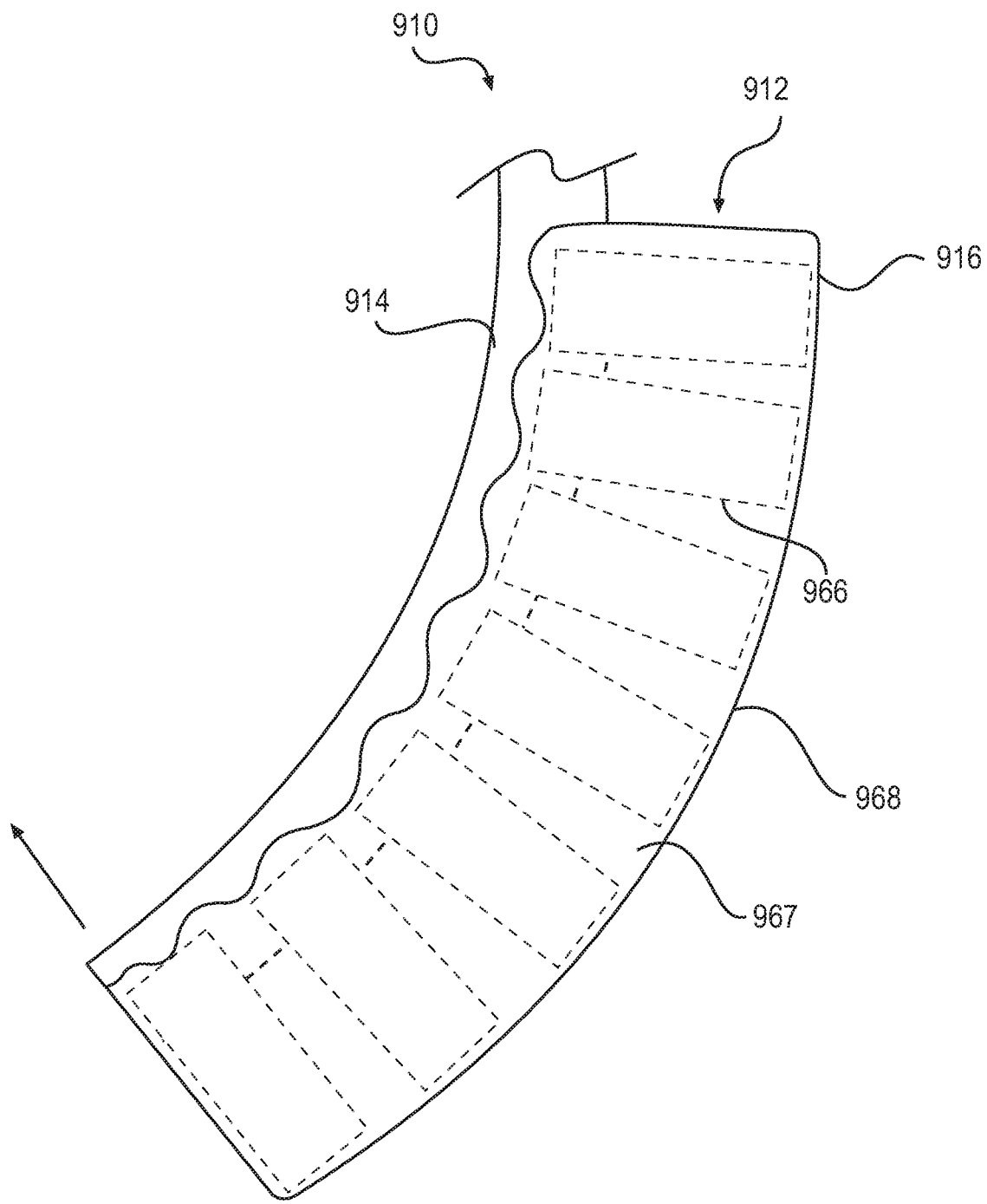
FIG. 10D is a side view of the clamp of FIGS. 10A-10C, with features for deflecting the clamp, in accordance with aspects of the present disclosure.

Additionally or alternatively, clamp 912 may be deflected to adapt to a shape of a subject's anatomy. For example, clamp 912 may be deflected to mimic the lesser curvature of a subject's stomach, as shown in FIG. 10D. Shaft 914 may be deflectable, and may include one or more steering wires (not shown) therein for imparting deflection forces. When clamp 912 is deflected, the spacing between portions of support members 966 closer to shaft 914 may be smaller than the spacing between portions of support members 966 farther from shaft 914. Portions of flexible sleeve 968 closer to shaft 914 may bend or fold, while portions of flexible sleeve 968 further from shaft 914 may be less bent or folded, or fully extended. Similar movements of shaft 914, flexible sleeve 968, and support members 966 may take place when clamp 912 is deflected in the opposite direction, or in one or more perpendicular directions.

Sleeve Gastrectomy

FIGS. 11A-11E show a method of forming a gastric sleeve in a subject using a surgical device 1010. Surgical device 1010 may include a shaft 1014 and clamp 1012. Clamp 1012 may include a first jaw member 1016 and a second jaw member 1018, and may define a central passage 1020 and an opening 1019 into central passage 1020. Surgical device 1010 may be similar to any of surgical devices 10, 110, 210, 310, 410, 510, 610, 710, 810, 910, and/or any other surgical devices described herein.

As shown in FIG. 11A, surgical device 1010 may be inserted into the stomach 1070 via the esophagus 1072. An introducer (not shown), such as an endoscope, may be inserted into esophagus 1072 and/or stomach 1070 along with surgical device 1010. In one example, the introducer may be inserted first, and surgical device 1010 may be inserted into the introducer, and then extended distally from the introducer to the target area. The introducer may include an imaging device that allows a user to visualize esophagus 1072 and/or stomach 1070, and surgical device 1010 during the procedure. Surgical device 1010 may be inserted to position clamp 1012 at or against the lesser curvature 1074 of stomach 1070.

Optionally, the length, width, and/or straightness (curvature) of clamp 1012 may be adjusted by the user. For example, clamp 1012 may be contracted or extended to a length that may provide the desired length for the resulting gastric sleeve. The contraction or extension of length may, for example, be carried out in the manner shown in FIGS. 10A-10C. In some instances, the user may set the length of clamp 1012 to be equal to the length of stomach 1070 between the lower esophageal sphincter 1078 and the pylorus 1076. In other instances, the user may set the length of clamp 1012 to be longer than the length of stomach 1070 between the lower esophageal sphincter 1078 and the pylorus 1076, with only a portion of clamp 1012 within the stomach being used to cut stomach 1070. Additionally or alternatively, clamp 1012 may be contracted or extended to a width that may provide the desired width for the resulting gastric sleeve. The contraction or extension of width may, for example, be carried out in the manner shown in FIGS. 9A and 9B. Additionally or alternatively, clamp 1012 may be deflected in the manner shown in FIG. 10D to provide the desired shape for the resulting gastric sleeve (for example, a shape that follows the contour of lesser curvature 1074).

Additionally or alternatively, the user may be provided with a kit having a plurality of surgical devices, each with a fixed length, width, and curvature, wherein the length, width, and/or curvature of each of those surgical devices differs from the length, width, and/or curvature of the other surgical devices. The user may select the appropriate surgical device from the kit to fit a subject's anatomy, rather than adjusting a surgical device to fit the subject's anatomy.

As shown in FIGS. 11B and 11C, a portion of stomach 1070 along a greater curvature 1080 may be guided toward opening 1019, and internalized through opening 1019 into central passage 1020. This insertion of the portion of stomach 1070 may be carried out in the manner shown in one or more of FIGS. 4, 5A, 5B, 6, 7A, 7B, 8A, and 8B, resulting in inversion of the portion of stomach 1070. In one example, the portion of stomach 1070 may be inserted starting with its distal end and working proximally, eventually ending with its proximal end. By inserting the distal end first and moving proximally therefrom, visualization of the insertion process from esophagus 1072 or a proximal region of stomach 1070 may remain unobstructed, giving the user a better view for confirming that the portion of stomach 1070 is internalized correctly and completely. With this process, the portion of stomach 1070 may be internalized without puncturing stomach 1070.

With the portion of stomach 1070 in central passage 1020 and opening 1019, clamp 1012 may be moved toward the closed configuration. The closing movement may be carried out in the manner shown in one or more of FIGS. 1A, 1B, 2A, 2B, 3A, 3B, 8A, and 8B. The single closing movement may clamp, cut, and seal the portion of stomach 1070 that lies within opening 1019. As outlined above, magnetic attraction, electrosurgery, and/or ultrasound may be used to facilitate cutting. Sealing of the cut may be carried out in the manner shown in FIG. 8B, and may be facilitated by magnetic attraction, electrosurgery, and/or ultrasound, as outlined above. With one step of closing clamp 1012, clamping, cutting, and sealing can be performed, thereby forming a gastric sleeve 1082 with a fully sealed side. The cut portion of stomach 1070 within central passage 1020 may be removed via, for example, esophagus 1072, as shown in FIG. 11D, leaving the completed gastric sleeve 1082 shown in FIG. 11E.

It will be apparent to those skilled in the art that various modifications and variations can be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:
1. An apparatus for treating tissue, comprising:
   a tube including:
      a slot extending longitudinally along a first side of the tube,
      a first jaw member on a first side of the slot, and
      a second jaw member on a second side of the slot; and
   a shaft coupled to the tube along a second side of the tube, wherein the first jaw member is movably coupled to the shaft, such that the first jaw member is movable toward the second jaw member to converge tissue within the slot and cut the tissue within the slot;
   a first strip coupled to the first jaw member, the first strip including a first engaging surface defining the first side of the slot;
   a second strip coupled to the second jaw member, the second strip including a second engaging surface defining the second side of the slot, wherein the first strip is detachable from the first jaw member, and the second strip is detachable from the second jaw member;
   wherein the tube is movable between an extended configuration, in which the tube has a first longitudinal length of an entirety of the tube, and a contracted configuration, in which the tube has a second longitudinal length of the entirety of the tube, the second longitudinal length being shorter than the first longitudinal length;
   wherein the tube is extendable in a proximal or distal direction along a central longitudinal axis of the tube; and wherein the shaft extends to a distal end of the first jaw member and a distal end of the second jaw member in the extended configuration and in the contracted configuration.

2. The apparatus of claim 1, wherein the first strip includes a protrusion protruding from the first engaging surface, wherein the protrusion includes at least one sharp edge configured to cut tissue, and wherein the second strip includes a recess shaped and sized to receive the protrusion.

3. The apparatus of claim 2, wherein a length of the protrusion is equal to a length of the first strip, and a length of the recess is equal to a length of the second strip.

4. The apparatus of claim 3, wherein the length of the first strip is equal to a length of the first jaw member, the length of the second strip is equal to a length of the second jaw member, the first jaw member is curved towards the second jaw member, and the second jaw member is curved towards the first jaw member.

5. The apparatus of claim 1, wherein the tube is deflectable from a straight configuration to a curved configuration.

6. The apparatus of claim 1, wherein at least one of the first jaw member and the second jaw member includes an electrode.

7. The apparatus of claim 1, further including at least one grasping assembly, wherein the grasping assembly includes a base coupled to the shaft, a grasping element, and a strand extending between the base and the grasping element, and the grasping element is configured for deployment via pressurized gas from the base through the slot, wherein the grasping element is configured to move radially outward from the shaft during deployment.

8. The apparatus of claim 1, further including at least one of a nozzle configured to deploy magnetic paint, and a magnet on an interior surface of the tube.

9. The apparatus of claim 1, wherein the first jaw member includes a plurality of curved, rigid support members extending radially-outward from a longitudinal axis of the shaft, and a sleeve supported by the plurality of support members, wherein each of the plurality of curved, rigid support members is longitudinally spaced from at least one other curved, rigid support member of the plurality of curved, rigid support members in the extended configuration.

10. An apparatus for treating tissue, comprising: a tubular member including: an opening extending longitudinally along a first side of the tubular member, a curved first side portion extending circumferentially about a central longitudinal axis of the tubular member and having a detachable first engaging surface, wherein the detachable first engaging surface extends along a first side of the opening, and a curved second side portion extending circumferentially about a central longitudinal axis of the tubular member and having a detachable second engaging surface, wherein the detachable second engaging surface extends along a second side of the opening; and a shaft coupled to the tubular member at a second side of the tubular member, wherein the first side portion is movably coupled to the shaft, such that the first side portion is movable toward the second side portion to move the detachable first engaging surface toward the detachable second engaging surface to converge tissue, and cut the tissue, and wherein a protrusion is fixed to and immovably coupled to the detachable first engaging surface, and the detachable second engaging surface includes a recess complementary to the protrusion; wherein a length of the protrusion is equal to a length of the detachable first engaging surface; wherein a length of the recess is equal to a length of the detachable second engaging surface; and wherein the protrusion includes at least one sharp edge, configured to cut tissue, extending the length of the detachable first engaging surface.

11. The apparatus of claim 10, wherein the detachable first engaging surface is part of a first strip that is removably attached to a surface of the first side portion, and the detachable second engaging surface is part of a second strip that is removably attached to a surface of the second side portion; wherein the first strip is ferromagnetic, and the second strip comprises a material that is magnetically attracted by the first strip.

12. The apparatus of claim 10, wherein the first side portion includes a first concave surface facing the second side portion, and wherein the second side portion includes a second concave surface facing the first side portion.

13. The apparatus of claim 10, wherein the protrusion is fixedly coupled to the detachable first engaging surface.

* * * * *